(12) United States Patent
Cannady

(10) Patent No.: US 8,042,687 B2
(45) Date of Patent: Oct. 25, 2011

(54) HEMOSTATIC CLIP CARTRIDGE

(75) Inventor: Freddy R. Cannady, Mebane, NC (US)

(73) Assignee: Vesocclude Medical LLC, Raleigh, NC (US)

( * ) Notice: Subject to any disclaimer, the term of this patent is extended or adjusted under 35 U.S.C. 154(b) by 523 days.

(21) Appl. No.: 12/136,593

(22) Filed: Jun. 10, 2008

(65) Prior Publication Data
US 2009/0152147 A1 Jun. 18, 2009

Related U.S. Application Data

(63) Continuation-in-part of application No. 12/002,201, filed on Dec. 14, 2007, now abandoned.

(51) Int. Cl.
B65D 85/24 (2006.01)
(52) U.S. Cl. .......................................... 206/339
(58) Field of Classification Search ............ 606/139, 606/142, 143, 151, 157, 219–221; 227/175.1, 227/176.1; 206/338–340, 363
See application file for complete search history.

(56) References Cited

U.S. PATENT DOCUMENTS

| | | | |
|---|---|---|---|
| 3,326,216 A | 6/1967 | Wood | 128/325 |
| 3,363,628 A | 1/1968 | Wood | 128/325 |
| 3,713,533 A | 1/1973 | Reimels | 206/56 |
| 4,076,120 A | 2/1978 | Carroll et al. | 206/339 |
| 4,146,130 A | 3/1979 | Samuels et al. | 206/340 |
| 4,212,390 A | 7/1980 | Raczkowski et al. | 206/339 |
| 4,294,355 A | 10/1981 | Jewusiak et al. | 206/339 |
| 4,361,229 A * | 11/1982 | Mericle | 206/339 |
| 4,696,396 A | 9/1987 | Samuels | 206/339 |
| 4,936,447 A | 6/1990 | Peiffer | 206/339 |
| 4,961,499 A | 10/1990 | Kulp | 206/339 |
| 4,972,949 A * | 11/1990 | Peiffer | 206/339 |
| 5,279,416 A | 1/1994 | Malec et al. | 206/339 |
| 5,908,430 A | 6/1999 | Appleby | 606/157 |
| 6,044,971 A | 4/2000 | Esposito et al. | 206/339 |
| 6,880,699 B2 | 4/2005 | Gallagher | |

* cited by examiner

Primary Examiner — Melanie Tyson
(74) Attorney, Agent, or Firm — The Eclipse Group LLP; Kevin E. Flynn

(57) ABSTRACT

Hemostatic clip cartridge having a plurality of individual compartments for holding preformed hemostatic clips. Each individual compartment progressively increases in width from the centerline of the cartridge. Flexible retaining fingers extend into each individual compartment and secure the hemostatic clip to a pedestal. Harvesting the hemostatic clip from that particular individual compartment by a clip applicator moves at least one of the retaining fingers from a first position to a post-harvest position. Subsequent removal of the clip applicator with the harvested hemostatic clip from that particular individual compartment leaves at least one of the retaining fingers in the post-harvest position different from the first position so that the post-harvest position of the at least one of the retaining fingers indicates that the particular individual compartment has been accessed by the clip applicator.

16 Claims, 11 Drawing Sheets

HEMOSTATIC CLIP CARTRIDGE

This application is a Continuation-in-Part of and claims priority to U.S. patent application Ser. No. 12/002,201 filed Dec. 14, 2007 for Hemostatic Clip Cartridge.

BACKGROUND

1. Field of the Disclosure

This disclosure relates generally to hemostatic clips used to ligate or clamp blood vessels during surgical procedures and more particularly, to a cartridge for securely retaining a plurality of preformed hemostatic clips prior to the withdrawal of the clips by a clip applicator. Even more particularly, the disclosure relates to a cartridge where the cartridge has a feature that is altered by the clip loading into the applicator process resulting in a pronounced visible indicator that the applicator has been inserted and removed from the individual compartment.

2. Related Art

Hemostatic clips are a well known practice and have been used in surgery for over 75 years in the strangulation of blood vessels and other fluid ducts. The clips are permanently implanted in the body and are typically formed in a "V" or "U" shape as described in Wood—U.S. Pat. Nos. 3,326,216 and 3,363,628. Regardless of shape, the basic clip has two legs originating from a central apex.

In a prior art cartridge, Peiffer—U.S. Pat. Nos. 4,936,447 and 4,972,949, a plurality of clips is retained in place on a center, fixed pedestal by flexible retaining fingers pressing against the exterior surface of the clips legs. The use of flexible fingers was advantageous in that it provided an effective way of securing the clip and allowed the user to load clips into the applicator using a single hand. The use of retaining fingers to secure the clip results in a portion of the clip being obscured by the retaining fingers and the user can not easily determine if a clip is present in the individual compartment. Clip detection is further impeded by the use of flexible fingers that return to their original location after a clip is removed by an applicator and the small size of the clips used to ligate vessels. Clip detection is further impeded by the individual compartment design which is purposely narrow to control applicator position and alignment with the clip during the clip loading into the applicator process. The prior art does not provide for a pronounced cartridge feature change resulting from the clip loading into the applicator process. Absence of a pronounced cartridge feature change creates a user nuisance as the user must closely inspect the cartridge prior to loading a clip and ensure a clip is present in the individual compartment. Failure to confirm clip presence could result in user nuisance due to wasted time as the user attempts to pick up a clip from an empty individual compartment, a worse scenario of the user believing they had picked-up and retracted a clip only to notice it missing at time of application, thus delaying the procedure while the user searches for the "lost" clip in the patient which they will never find, or the worst scenario of causing patent injury where the user, who erroneously thinks they have picked up a clip, closes an empty applicator on a vessel resulting in an unplanned severance of the vessel. To compensate for the lack of a pronounced cartridge feature change, the prior art provided for such a cartridge wherein the base is made of a light colored material and the retaining fingers are made of a dark colored material to help facilitate detection of empty individual compartments.

In Reimels—U.S. Pat. No. 3,713,533, a plurality of "V" shaped clips is retained in place on a center, fixed pedestal by placing the ends of the clips under the shoulder of housing. The use of the housing was advantageous in that it provided an effective way of securing the clip and it allowed the ability for the user to load clips into the applicator using a single hand. Using the clip ends to secure the clip does not result in a pronounced cartridge feature change as part of the clip loading into the applicator process and the user can not easily determine if a clip is present in the slot due to the small size of the clips. Clip detection is further impeded by the individual compartment design which is purposely narrow to control applicator position and alignment with the clip during the clip loading into the applicator process. Absence of a pronounced cartridge feature change creates a user nuisance as the user must closely inspect the cartridge prior to loading a clip and ensure a clip is present in the individual compartment.

In Wood—U.S. Pat. No. 3,326,216, a plurality of clips is retained by press fitting the clip over a rigid, fixed pedestal with the resulting friction force on the internal surface of the clip securing the clip to the cartridge. Although the complete clip exterior is exposed, the small size of the clip does not provide an easily detectable method to determine if a clip had been previously removed and no pronounced cartridge feature change occurs as part of the clip loading into the applicator process. The user must closely inspect the cartridge prior to loading a clip and ensure a clip is present in the individual compartment. Clip detection is further impeded by the individual compartment design which is purposely narrow to control applicator position and alignment with the clip during the clip loading into the applicator process.

In other prior art such as Carroll et al. —U.S. Pat. No. 4,076,120, Samuels et al.—U.S. Pat. No. 4,146,130, Raczkowski et al. —U.S. Pat. No. 4,212,390, Samuels—U.S. Pat. No. 4,696,396, Kulp—U.S. Pat. No. 4,961,499, Appleby—U.S. Pat. No. 5,908,430, and Esposito et al. —U.S. Pat. No. 6,044,971, a plurality of clips is held in place by the legs, face or top of the clip contacting features formed into the clip compartment walls The use of a clip compartment wall feature to secure the clip impedes clip detection by adding an additional feature to the individual compartment which is purposely narrow to control applicator position and alignment with the clip during the clip loading into the applicator process. In all cases, no pronounced cartridge feature change occurs as part of the clip loading into the applicator process and the user can not easily determine if a clip is present in the slot due to the small size of the clip. Absence of a pronounced cartridge feature change creates a user nuisance as the user must closely inspect the cartridge prior to loading a clip and ensure a clip is present in the individual compartment.

In Jewusiak et al.—U.S. Pat. No. 4,294,355, a plurality of clips is held in place by a film secured by a cover plate to hold clips in place. This film is weakened along the centerline of the clips. As the applicator is inserted into an individual compartment, it ruptures the film so the clip can be removed. A film or tape covering to secure clips is also present in Samuels et al.—U.S. Pat. No. 4,146,130. The use of film/tape may create a cartridge feature change as part of the clip loading into the applicator process, but without a feature to lock the ruptured film/tape in a new location the inherit memory of film/tape may result in the film/tape returning to its original location thus obscuring the individual compartment and making it difficult to detect an empty individual compartment. The prior art does not provide for a locking feature. Clip detection is further impeded by the individual compartment design which is purposely narrow to control applicator position and alignment with the clip during the clip loading into the applicator process. The use of film/tape creates other concerns. In a later patent, Samuels—U.S. Pat. No. 4,696,396, by the same inventor as U.S. Pat. No. 4,146,130, the inventor describes a problem with tape. According to this second patent the tape described in the first patent may stick to the clip when the clip is being removed. Additionally, the use of film/tape may generate particulate as part of the rupture process increasing the potential of placing film/tape particulate in the patient.

In Mericle—U.S. Pat. No. 4,361,229, a plurality of plastic clips with bosses is held in place by fingers on the side of the cartridge that engage the clip bosses and operates in principle very similar to Peiffer—U.S. Pat. No. 4,936,447. The use of retaining fingers to secure the clip results in a portion of the clip being obscured by the retaining fingers and the user can not easily determine if a clip is present in the individual compartment. Clip detection is further complicated by the use of flexible fingers that return to their original location after a clip is removed by an applicator. Clip detection is further impeded by the individual compartment design which is purposely narrow to control applicator position and alignment with the clip during the clip loading into the applicator process. The prior art does not provide for a pronounced cartridge feature change resulting from the clip loading into the applicator process and the small size of the clips. The user must closely inspect the cartridge prior to loading a clip and ensure a clip is present in the individual compartment.

In Malec et al.—U.S. Pat. No. 5,279,416, a plurality of clips is held in place by a retaining member which engages the clip ends and secures the clip in the cartridge When the applicator engages the clip, the retaining member is displaced creating a cartridge feature change. The use of individual retaining members (i.e. one per clip) creates a complex multiple piece cartridge design and increases manufacturing cost. The cartridge feature change is not pronounced as it occurs in the bottom of the individual compartment which is purposely narrow to control applicator position and alignment with the clip during the clip loading into the applicator process. The user can not easily determine if a clip is present in the slot due to the small size of the clips used to ligate vessels. The user must closely inspect the cartridge prior to loading a clip and ensure a clip is present in the individual compartment.

It is thus apparent that there is a need in the art for an improved system for transporting and supplying preformed hemostatic clips, specifically a system where the hemostatic clip cartridge has a pronounced feature change created by the clip loading into the applicator process. This pronounced feature change allowing the user to easily determine that the applicator has been previously inserted into the individual compartment thus removing the need for the user to closely inspect the cartridge for clip presence in the individual compartment.

SUMMARY

Aspects of the teachings contained within this disclosure are addressed in the claims submitted with this application upon filing. Rather than adding redundant restatements of the contents of the claims, these claims should be considered incorporated by reference into this summary.

Improvements to the prior art may be realized with a hemostatic clip cartridge having a plurality of individual compartments, each of which will hold one hemostatic clip. In one implementation of teachings of the present disclosure, each individual compartment is dimensioned from the center out so as to progressively increase in width providing a pair of compartment side walls to control clip position, a pair of compartment side walls to align the applicator with the hemostatic clip during the clip loading into the applicator process, and a pair of compartment side walls with locking tabs creating a compartment significantly larger than the applicator to maximize visual detection when the locking tabs prevent the retaining fingers from returning to their original location after the clip loading into the applicator process. Each individual compartment has a center, fixed pedestal to position the hemostatic clip.

Each hemostatic clip is held in place by two retaining fingers that extend into the individual compartment and contact the hemostatic clip securing it to the pedestal. These retaining fingers are made of a flexible material that allows the applicator to move the retaining fingers as the applicator enters the individual compartment to pick up a hemostatic clip. The retaining fingers flex past the locking tabs during the clip loading into the applicator process yet have sufficient thickness and interference to prevent the retaining fingers from returning to their original position when the applicator is retracted.

Because the interference between the retaining finger and the locking tabs is minimized, only a small amount of force is required to place the applicator over a clip, thus a clip can be placed into an applicator (sometimes worded as "harvested") with one hand, yet tactile feedback is provided to the user.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Other systems, methods, features, and advantages of the disclosed teachings will be or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The various teachings of this disclosure may be better understood with reference to the following figures. The components in the figures are not necessarily to scale, emphasis instead being placed upon illustrating the principles to be conveyed. Moreover, in the figures, like reference numerals designate corresponding parts throughout the different views.

The above and other objects, features, and advantages of the various conveyed teachings will be better understood by reading the following more particular description presented in conjunction with the following drawings, wherein.

DETAILED DESCRIPTION

The following description is of the best presently contemplated mode of carrying out the teachings of the present disclosure. This description is not to be taken in a limiting sense but is made merely for the purpose of describing the general principles to one of ordinary skill in the art. The scope of the patent protection should be determined by referencing the appended claims.

Figure 1:
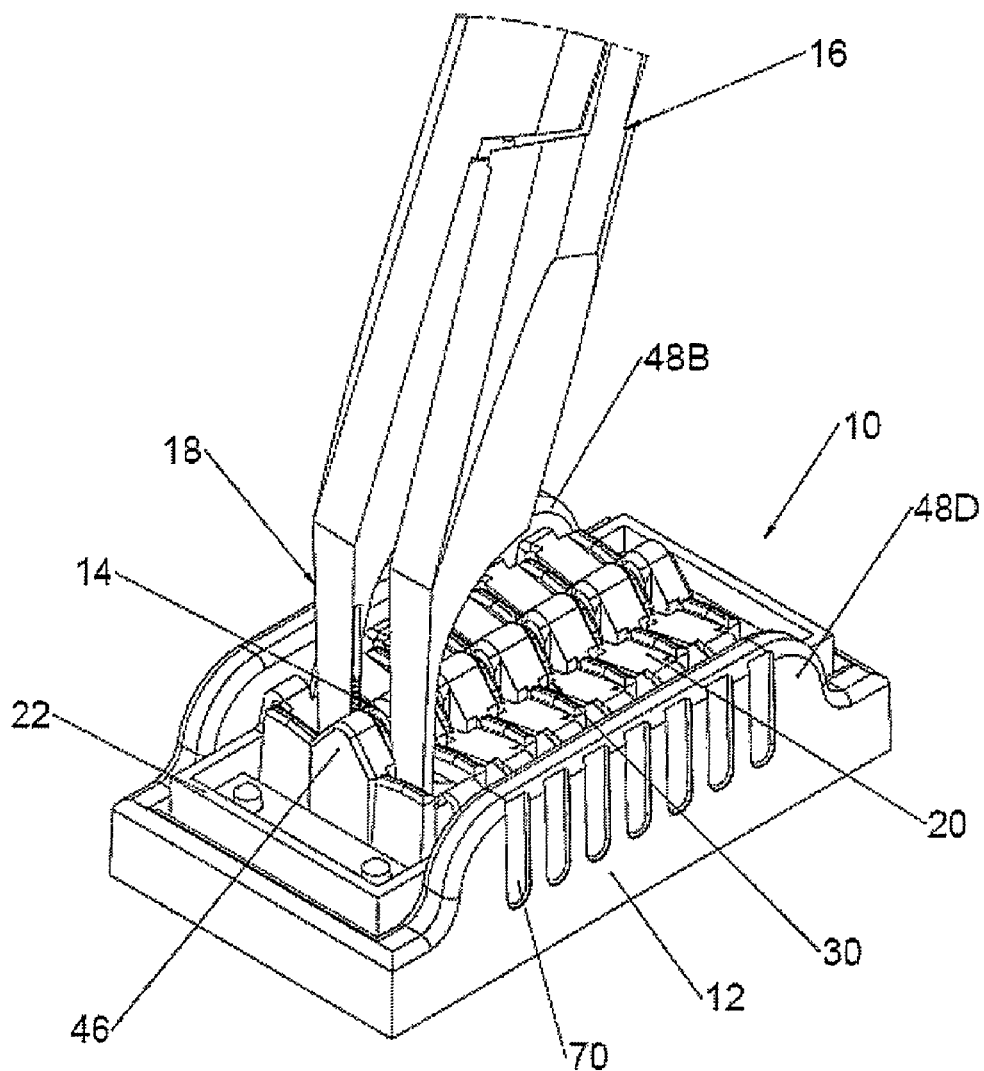
FIG. 1 shows a perspective view of the cartridge with an applicator inserted therein.
Figure 3:
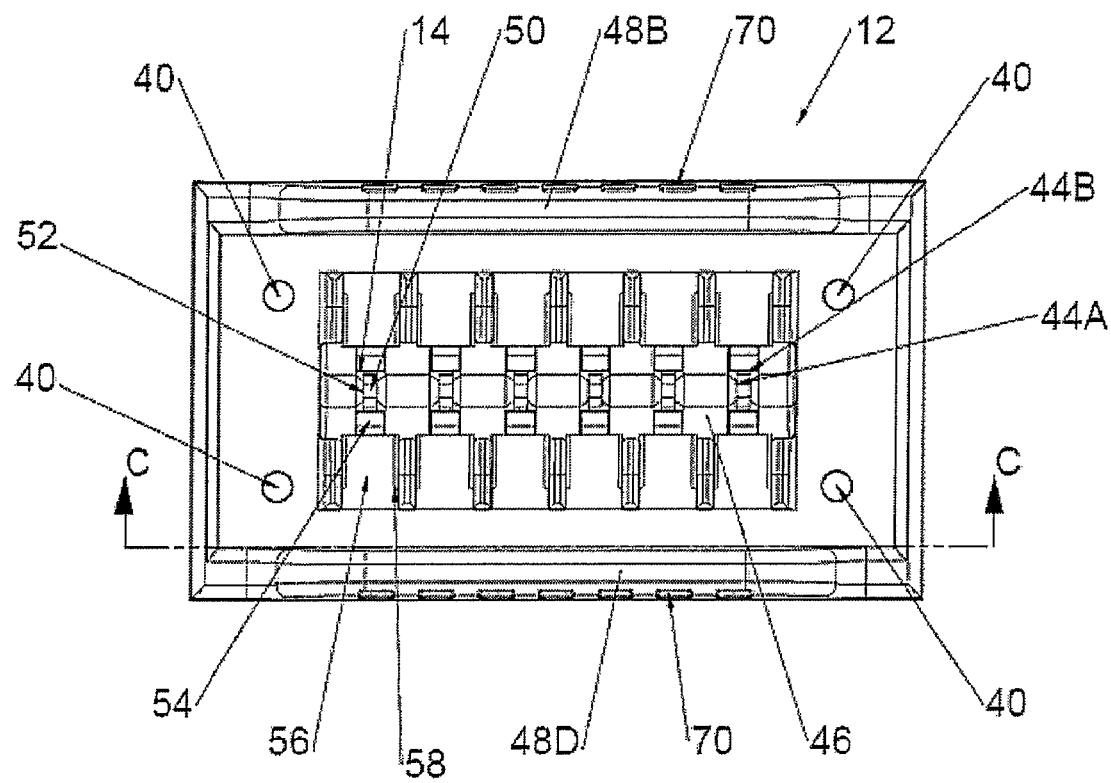
FIG. 3 is a top view of the base component.

FIG. 1 shows a perspective view of the cartridge with an applicator positioned over a clip in one of the individual compartments. Referring now to FIG. 1, a cartridge 10 (also called a hemostatic clip cartridge) is shown having a base component 12. Formed into the base component 12 is a plurality of individual compartments 14, separated by compartment walls 46. Each of the individual compartments 14 will hold one hemostatic clip 30. Each individual compartment 14 has three sub-compartments established by different width dimensions (as shown in FIG. 3). The centered clip sub-compartment 52 is dimensioned to control clip location. An applier sub-compartment 54 is positioned on each side of the clip sub-compartment and is dimensioned to control and align the applicator 16 with the hemostatic clip 30 during the clip loading into the applicator process. The locking sub-compartment 56 is positioned on each side of the applier sub-compartment 54 and is dimensioned to include locking tabs (discussed below) and creating a sub-compartment 56 significantly larger than the applier sub-compartment 54 to maximize visual detection when the locking tabs prevent the retaining fingers 20 from returning to their original location after the clip loading into the applicator process (as will be described in detail below). The hemostatic clips 30 are held on the cartridge 10 by a plurality of retaining fingers 20, which are attached to a rim 22. The cartridge 10 has two retaining fingers 20 for each individual compartment 14, one located on each side of the individual compartment 14.

Figure 11:
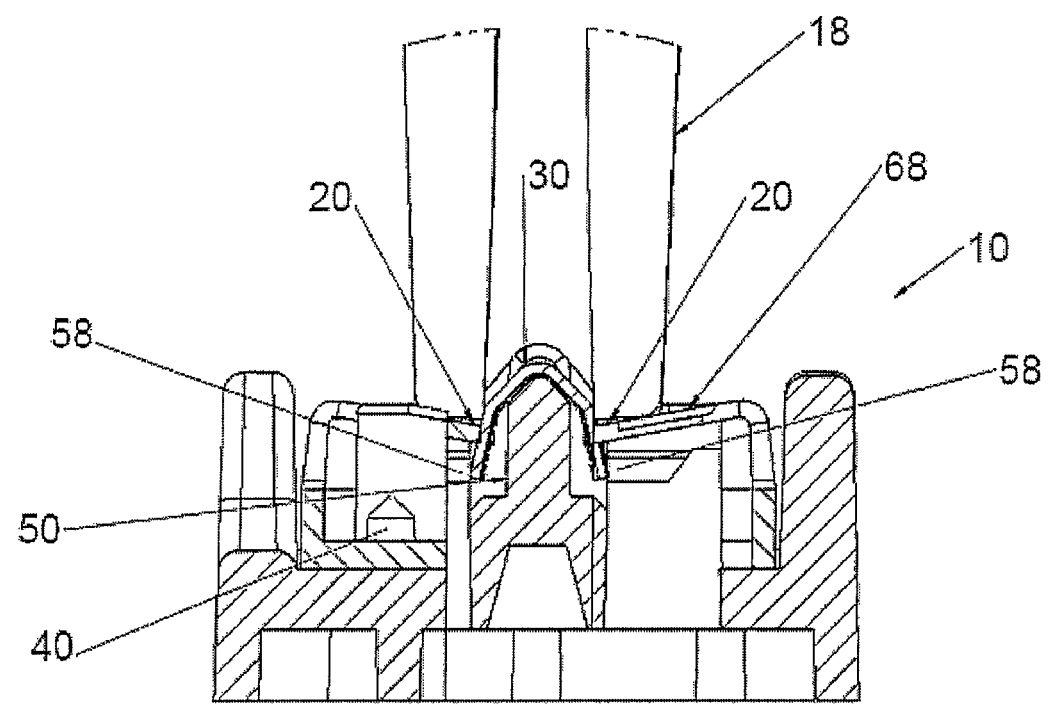
FIG. 11 is a section end view of the cartridge, taken through the line A-A of FIG. 8, showing an applicator positioned before insertion into the cartridge.
Figure 12:
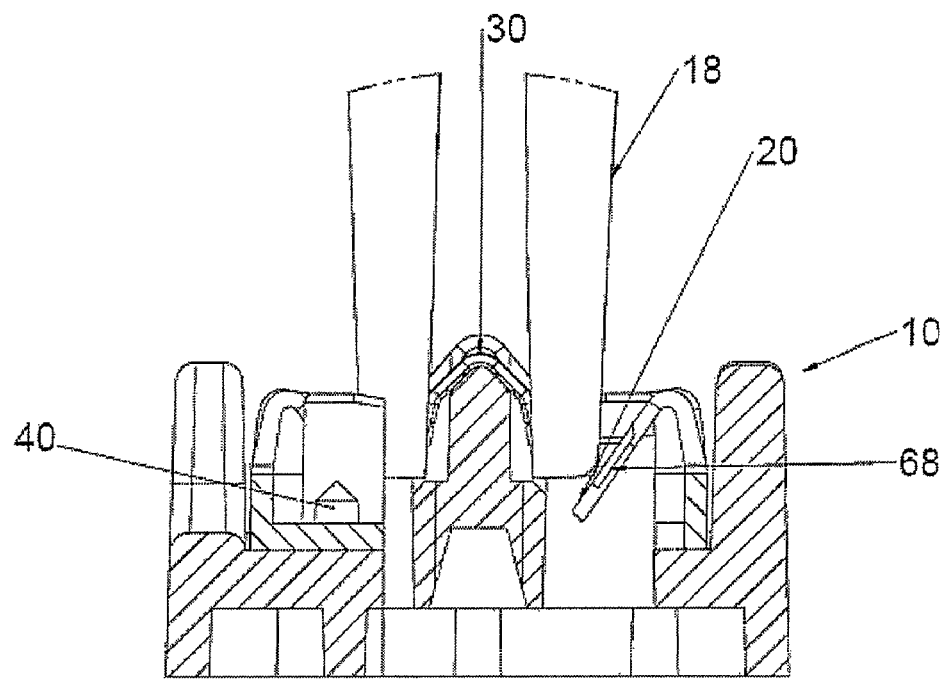
FIG. 12 is a section end view of the cartridge, taken through the line A-A of FIG. 8, showing an applicator fully inserted into the cartridge.

In operation, the applicator 16 is positioned over an individual compartment 14 and inserted downward into the individual compartment 14. As the applicator jaws 18 move downward, the retaining fingers 20 in the individual compartment 14 rotate down into the individual compartment 14 and away from the legs of the hemostatic clip 30. This is illustrated in FIG. 11 and FIG. 12 by the pair of retaining fingers 20 being pressed downward by the applicator jaws 18. The retaining fingers 20 are below the applicator jaws 18 and rotate away from the clip as the applicator jaws 18 are fully inserted into the individual compartment 14.

Visible in FIG. 1 are a set of grooves 70 on side wall 48D. Not visible in FIG. 1 but visible in FIG. 3 are a set of grooves 70 on the outside face of opposite side wall 48B. These sets of grooves 70 provide a textured surface to make the hemostatic clip cartridge 10 easier to hold while wearing gloves (especially if the gloves are wet from other activities related to the surgical procedure).

Figure 2A:
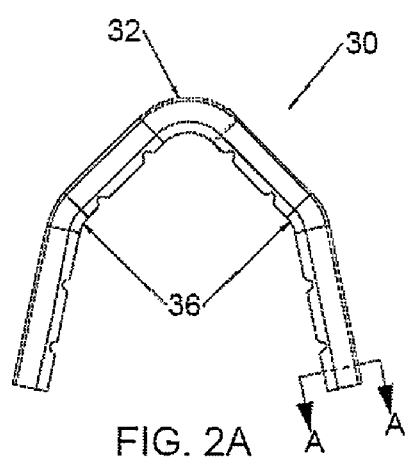
FIG. 2A is a side view of a prior art clip that may be used with a hemostatic clip cartridge using teachings of the present disclosure.
Figure 2B:
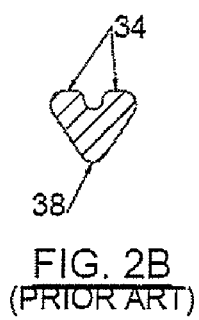
FIG. 2B is a section view of a prior art clip shown in FIG. 2A taken through the line A-A of FIG. 2A.

FIGS. 2A and 2B show a side view and an end view, respectively, of a prior art clip, described generally in Wood—U.S. Pat. No. 3,363,628, which is suitable for use with the present hemostatic clip cartridge and the Peiffer '447 hemostatic clip holder. Other clips are also suitable for use with the present disclosure, for example plastic clips having a retaining hook or snap closure will also work with the present disclosure. One of skill in the art will recognize that a hemostatic clip having outer dimensions that are different from the hemostatic clip used in the figures of the present disclosure might impact the dimensions of a hemostatic clip cartridge intended to hold and dispense such clips. However, a hemostatic clip cartridge sized to work with a different size of hemostatic clips could implement the teachings of the present disclosure.

FIG. 2A shows a side view of the hemostatic clip 30 which is formed by a central bend 32 creating two legs, each with a leg bend 36.

FIG. 2B shows an section view of the clip 30. The hemostatic clip occlusive surface 34 has a pair of rounded sections separated by a groove. The outside edge of the clip is generally triangular in shape, having a peak 38 to fit in the applicator.

FIG. 3 shows a top view of the base component 12 of the hemostatic clip cartridge 10 as shown in FIG. 1. Referring now to FIG. 3 the individual compartment 14 has three sub-compartments established by different width dimensions. The centered clip sub-compartment 52 is dimensioned to control clip location. An applier sub-compartment 54 is positioned on each side of the clip sub-compartment 52 and is dimensioned to control and align the applicator jaws 18 with the hemostatic clip 30 during the clip loading into the applicator process. The locking sub-compartment 56 is positioned on each side of the applier sub-component 54 and is dimensioned to include locking tabs (discussed below) and creating a locking sub-compartment 56 significantly larger than the applier sub-compartment 54 to maximize visual detection when the locking tabs prevent the retaining fingers 20 from returning to their original location after the clip loading into the applicator process. The base component 12 shown in FIG. 3 is generally rectangular in shape, and is typically molded from rigid material that can be sterilized for surgical use. The hemostatic clip cartridges 10 may be intended for a single cycle of loading with hemostatic clip 10 and then use. The hemostatic clips 30 may be loaded into the hemostatic clip cartridge 10 before the loaded cartridge is sterilized.

Alignment posts 40 may be used to center and attach the clip retaining component 60 (see FIG. 5). The clip sub-compartment 52 within each individual compartment 14 contains a pair of centering protrusions 44A and 44B to help center the clip (not shown) within the clip sub-compartment 52. The centering protrusions 44A and 44B are attached to the compartment walls 46 of the individual compartment 14 and also to a pedestal 50 (centering protrusions are best seen in FIG. 4).

Side walls 48B and 48D serve to protect the retaining fingers 20 from being prematurely depressed and create a pocket into which the clip retaining component 60 (FIG. 5A) is placed. FIG. 4 has side wall 48D removed but the two ends of side wall 48B are visible. Side walls 48B and 48D are also visible in FIG. 1.

Locking tabs 58 are positioned and toleranced to allow passage of the retaining finger 20 (FIG. 7B) during applicator jaw 18 (FIG. 1) insertion into individual compartment 14, but do not allow the retaining fingers 20 (FIG. 7C) to return to their original positions when the applicator is retracted. As noted below in relations to the discussion of FIG. 7B, the retaining finger 20 may be designed to include retaining finger wings 68 that flex when forced downward between the locking tabs 58. For precision, locking tabs 58 may be called compartment locking tabs 58.

Figure 4:
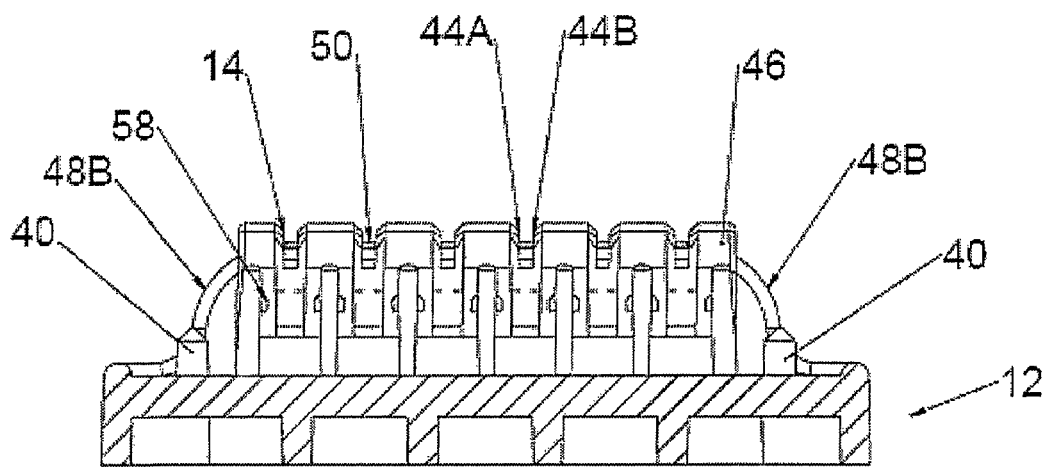
FIG. 4 is a side view of the base component.

FIG. 4 shows a side view of the base component 12. Referring now to FIG. 4, the base component 12 is shown, having the side wall 48B partially visible in this view as it is on the far side of the base component 12. The pedestal 50 is shown extending down through each individual compartment 14. The centering protrusions 44A and 44B extend down into the each individual compartment 14 below the top of the pedestal 50. The locking tabs 58 are positioned to allow passage of the retaining fingers 20 (FIG. 7B) during applicator insertion into pocket, but not allow the retaining fingers 20 (FIG. 7C) to return to their original position (above the locking tabs 58) when the applicator is retracted.

Figure 5A:
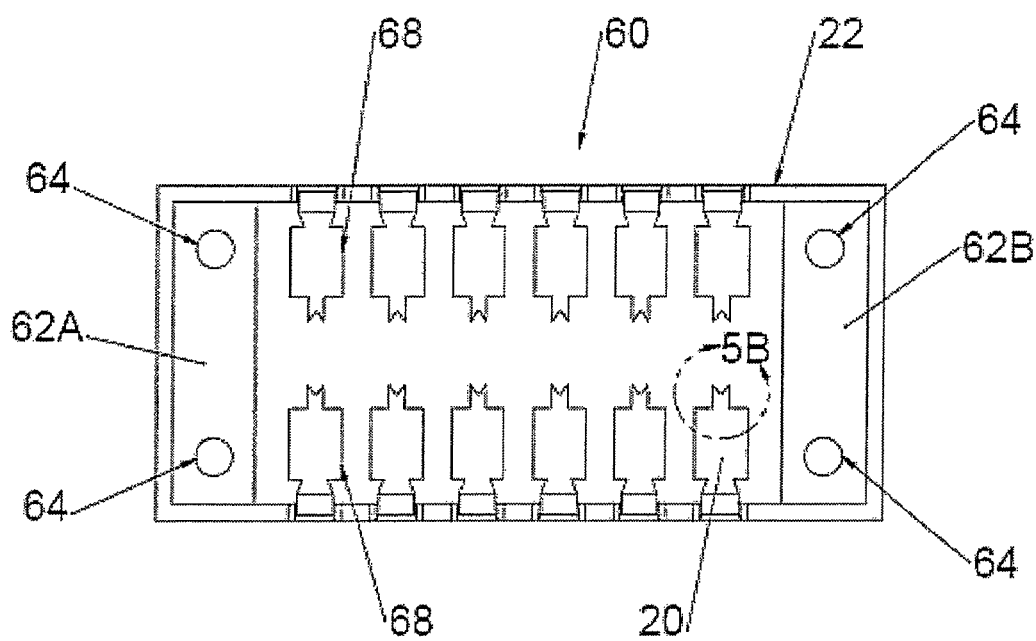
FIG. 5A is a top view of the clip retaining component.

FIG. 5A shows a top view of the clip retaining component 60 as implemented for use with the teachings of the present disclosure. Referring now to FIG. 5A, the clip retaining component 60 has a rim 22 and a plurality of retaining fingers 20 with retaining finger wings 68. The clip retaining component 60 is typically molded from flexible material that can be sterilized for surgical use. The rim 22 has one pair of retaining fingers 20 for each individual compartment 14 in the base component 12 (FIG. 1). A pair of horizontal support members 62A and 62B provides structural support for the rim 22 so that the rim 22 does not bend easily during the manufacturing process. Four post holes 64 are of a size, shape and location to allow them to mate with the alignment posts 40 of the base component 12 (FIG. 3). During the assembly process, the hemostatic clips 30 (FIG. 1) are placed in the individual compartments 14 (FIG. 3), and then the clip retaining component 60 is placed over the hemostatic clips 30 (FIG. 1), and the post holes 64 are aligned with the alignment posts 40 (FIG. 3). The clip retaining component 60 is then permanently attached to the base component 12 (FIG. 3) by reforming the alignments posts 40 (FIG. 3) to make the ends of the alignment posts larger than the post holes 64.

Figure 5B:
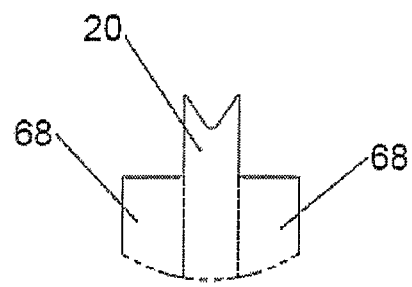
FIG. 5B is a detail from FIG. 5A showing an enlarged top view of a retaining finger.

FIG. 5B shows an enlarged view of the distal portion of a retaining finger 20. Referring now to FIG. 5B, the retaining fingers 20 contain two locking wings 68 which are dimensioned to flex and pass through the interference created with the locking tabs 58 (FIG. 7B) during applicator insertion into individual compartment 14, but not allow the retaining finger 20 to return to original position upon applicator retraction (FIG. 7C).

Figure 6:
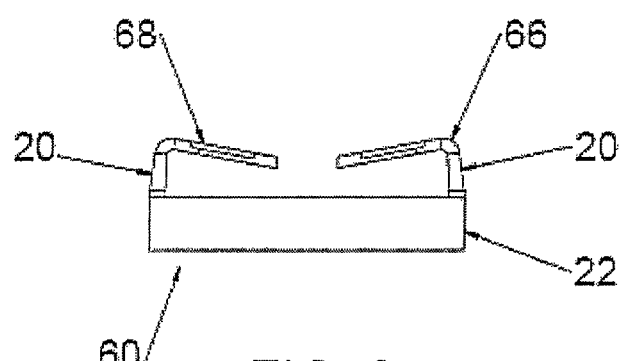
FIG. 6 is an end view of the clip retaining component.

FIG. 6 shows an end view of the clip retaining component 60. This figure illustrates the retaining finger bend 66 in the retaining fingers 20 which allows the retaining fingers 20 to slope downward toward the hemostatic clip 30 (FIG. 1). The retaining fingers could also be designed to be substantially horizontal after the retaining finger bend 66 rather than having a visibly downward slope.]

Figure 7A:
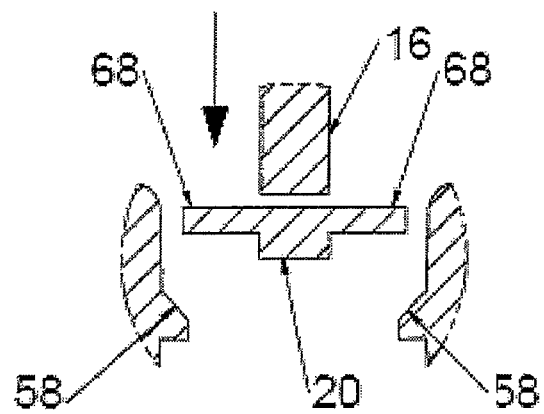
FIG. 7A, FIG. 7B and FIG. 7C show a section view of the retaining fingers 20 with respect to the locking tabs 58 before, during and after applicator insertion.
Figure 7B:
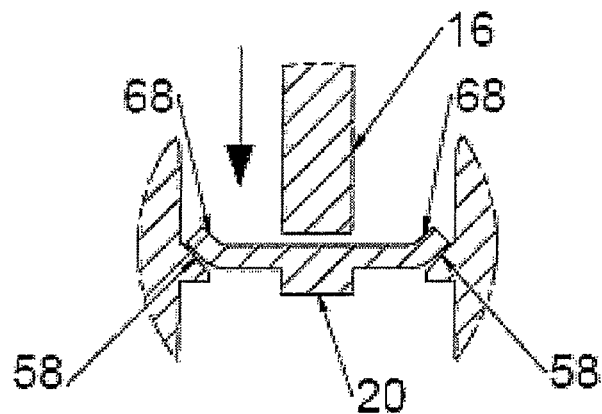
Figure 7C:
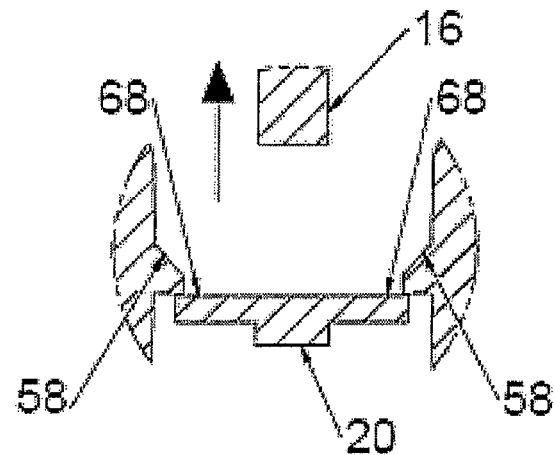

FIG. 7A, FIG. 7B and FIG. 7C show a section view of the retaining fingers 20 with respect to the locking tabs 58 prior to, during and after applicator insertion (applicator is represented by the general element number 16 rather than using the applicator jaw element number 18). Referring now to FIG. 7A, prior to applicator 16 insertion, the retaining fingers 20 are located above the locking tabs 58 (FIG. 7A). The thickness of the retaining finger wings 68 is dimensioned relative to retaining finger material characteristics to allow the retaining finger 20 to flex and pass through the interference created with the locking tabs 58 during applicator 16 insertion as shown in FIG. 7B, but not allow retaining fingers 20 to return to original position upon applicator 16 retraction as shown in FIG. 7C.

The retaining finger wings 68 can be thought of as finger locking tabs that extend outward from the longitudinal centerline of the retaining finger 20 but have in this implementation a reduced material thickness relative to the longitudinal centerline of the retaining finger 20 in order to make it easier for that portion of the retaining finger to flex past the locking tabs 58.

Figure 8:
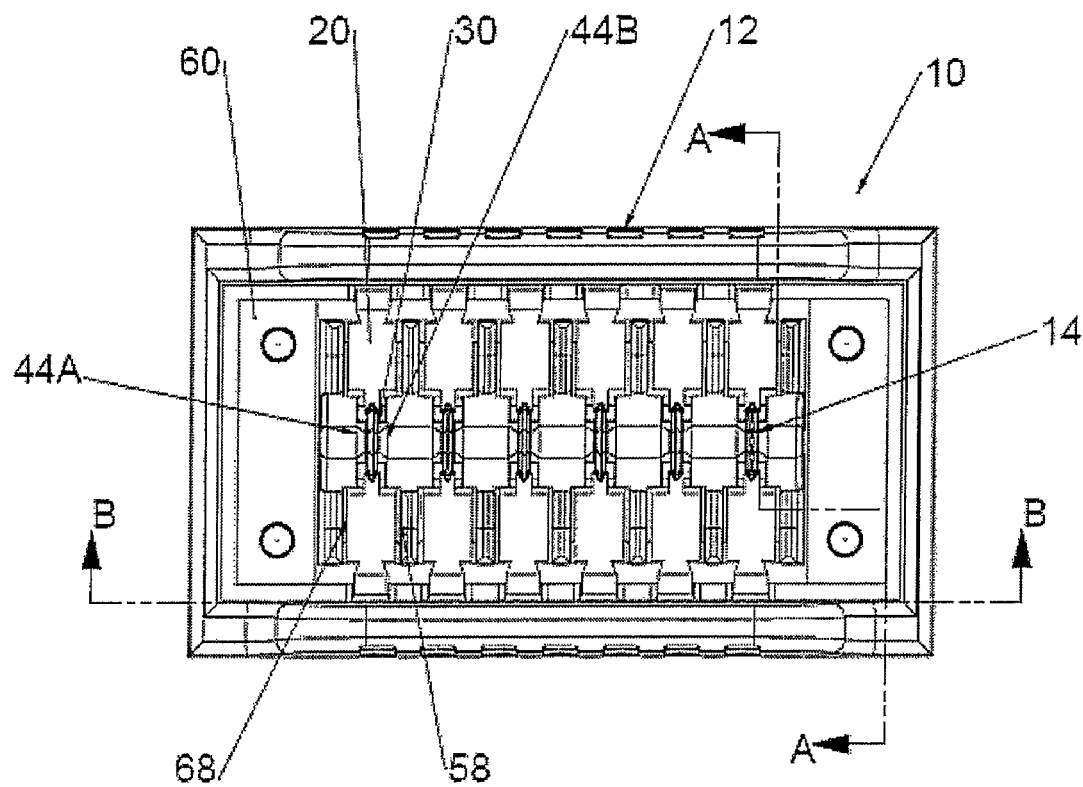
FIG. 8 is a top view of the cartridge showing clips contained therein.
Figure 9:
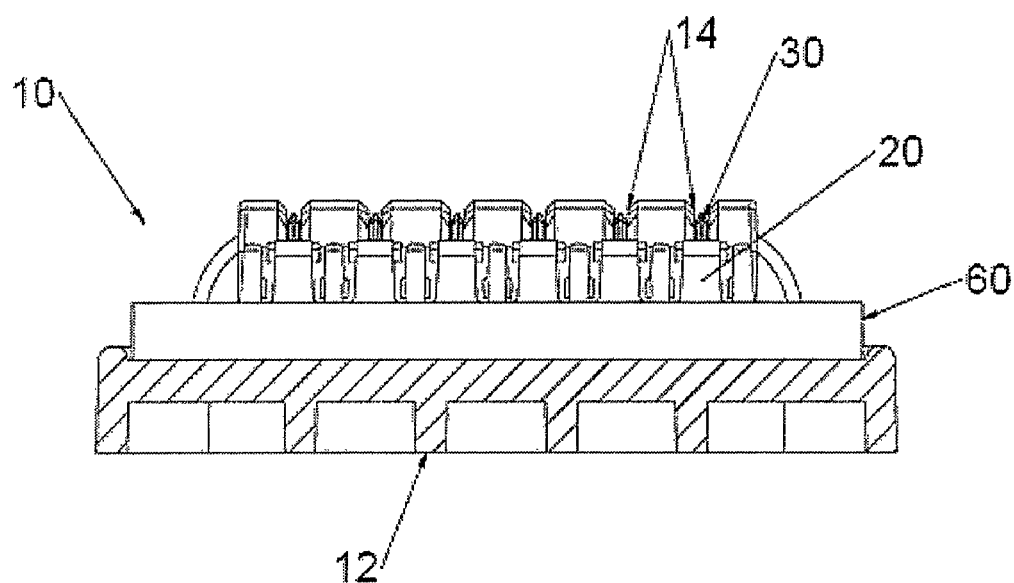
FIG. 9 is a section side view of the cartridge, taken through the line B-B of FIG. 8, showing the clip retaining component and clips assembled onto the base component.

FIG. 8 shows a top view of the cartridge 10, and FIG. 9 shows a side sectional view taken through the line B-B of FIG. 8. Referring now to FIGS. 8 and 9, the base component 12 is shown with individual compartments 14, each of which contains a hemostatic clip 30. The clip retaining component 60 is attached to the base component 12, and each of the retaining fingers 20 are positioned over a side of a hemostatic clip 30. FIG. 8 illustrates the end of the retaining finger 20 contacting the hemostatic clip 30 to hold the hemostatic clip 30 in place.

Figure 10:
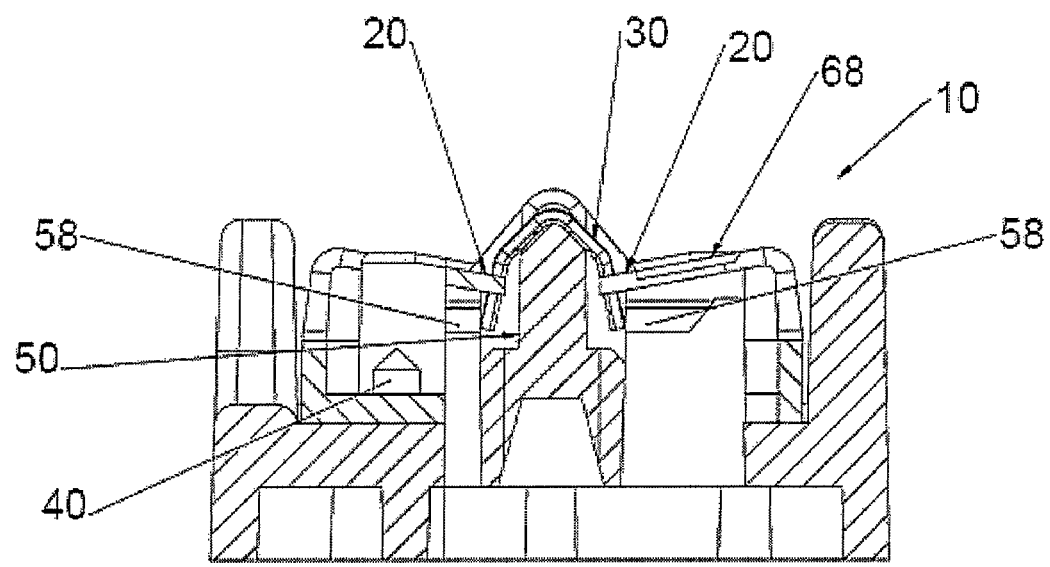
FIG. 10 is a section end view of the cartridge, taken through the line A-A of FIG. 8, showing a clip being retained by the retaining fingers.

FIG. 10 shows an end section view of the cartridge 10, taken through the line A-A of FIG. 8. Referring now to FIG. 10, the retaining fingers 20 are shown to be located above the locking tabs 58.

FIG. 11 shows an end section view of the cartridge 10, taken through the line A-A of FIG. 8. Referring now to FIG. 11, the applicator jaws 18 are being moved downward to be placed over a hemostatic clip 30 and the retaining fingers 20 are still positioned above the locking tabs 58 (as shown in FIG. 7A).

FIG. 12 shows an end section view of the cartridge 10, taken through the line A-A of FIG. 8. Referring now to FIG. 12, the applicator jaws 18 are fully in place over the hemostatic clip 30. The downward applicator force provided by the user to insert the applicator jaws 18 into the cartridge and over the hemostatic clip 30 pushes the retaining finger 20 past the locking tabs 58 (as shown in FIG. 7C). Also visible in FIG. 12 are alignment post 40 and retaining finger wing 68.

Figure 13:
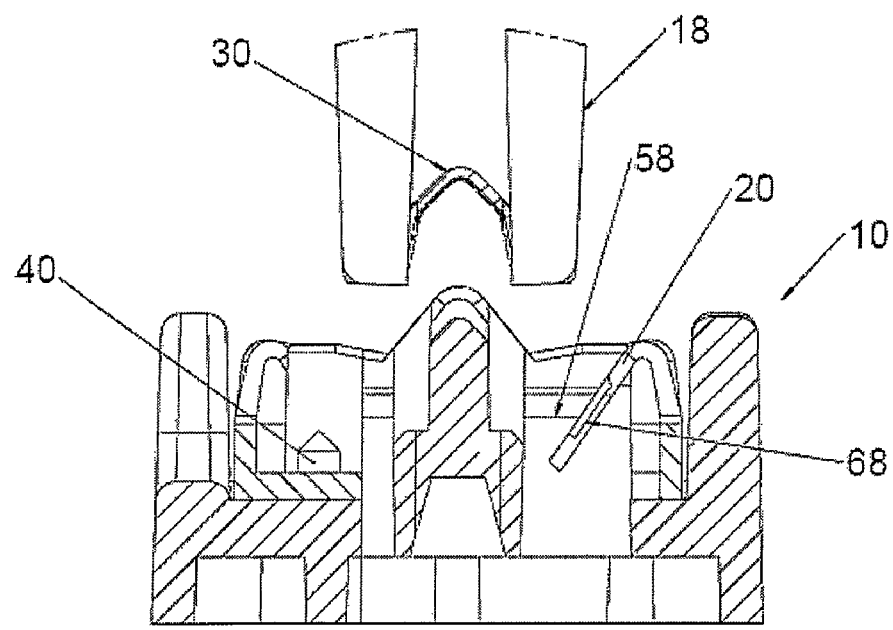
FIG. 13 is a section end view of the cartridge, taken through the line A-A of FIG. 8, showing the retaining fingers positioned below the locking tabs after an applicator has been fully inserted into and removed from the cartridge.

FIG. 13 shows an end section view of the cartridge 10, taken through the line A-A of FIG. 8. Referring now to FIG. 13, the applicator jaws 18 have been inserted into the individual compartment 14, picked up a hemostatic clip 30 and retracted so that the applicator jaws 18 are no longer in contact with the retaining fingers 20. Upon applicator retraction the retaining fingers 20 attempt to return to their original, pre-applicator insertion position (as shown in FIGS. 7A and 11), but are prevented from doing so by the locking tabs 58.

The retaining fingers 20 remain under the locking tabs 58 creating a pronounced, visible indicator that the applicator has been inserted into the individual compartment (visible indicator discussed below). The initial contact between the locking tab 58 and the retaining finger 20 created by the clip loading into an applicator process provides tactile feedback to the user that applicator insertion is in progress. In many implementations of the teachings of the present disclosure, the user will feel, and possibly even hear, the transition of the retaining finger wings 68 from flexed against the locking tabs 58 (as shown in FIG. 7B), to un-flexed but retained below the locking tabs 58 (as shown in FIG. 7C).

The teaching of having locking tabs 58 to prevent the retaining fingers 20 from returning to their original, pre-applicator insertion position is in direct contrast to the teaching of the Peiffer '447 patent which teaches in Col 10 lines 24 to 33:

"The flexible clip retainer fingers 20 move freely out of the way of the applicator 16 during the process of transferring the clip from the cartridge into the jaws of the applicator, thus insuring a smooth release of the applicator from the cartridge with the use of only one hand and without the use of any additional devices, such as a base weight. Since the fingers are resilient and attempt to return to their relaxed state, they act as a spring to help eject the applicator 16 from the cartridge 10."

Thus, the teachings of the present disclosure teach 180 degrees away from purported advantages in Peiffer '447 in order to provide a tactile indication to the user during the loading process that the applicator has been inserted sufficiently to press the retaining finger 20 past the locking tabs 58 and then providing a permanent and pronounced visual indicator by way of the latched retaining fingers 20 that indicates that the applicator has already acquired the clip from that individual compartment 14.

Figure 14:
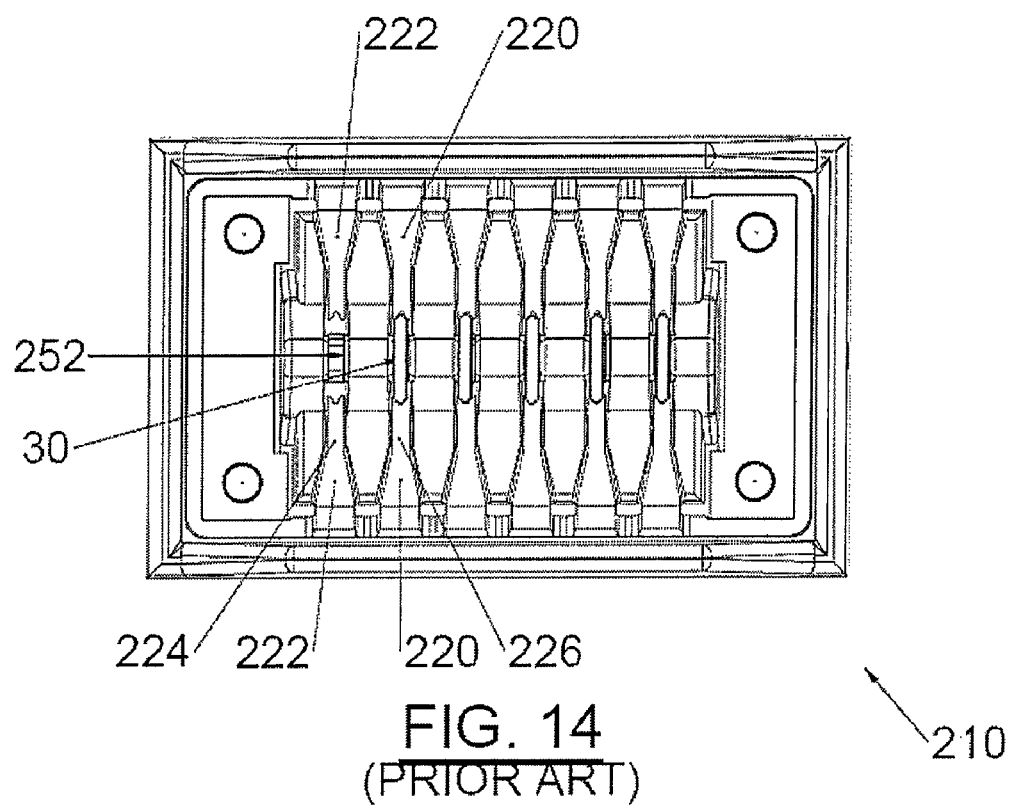
FIG. 14 is a top view of a Peiffer type hemostatic clip holder with one hemostatic clip removed.
Figure 15:
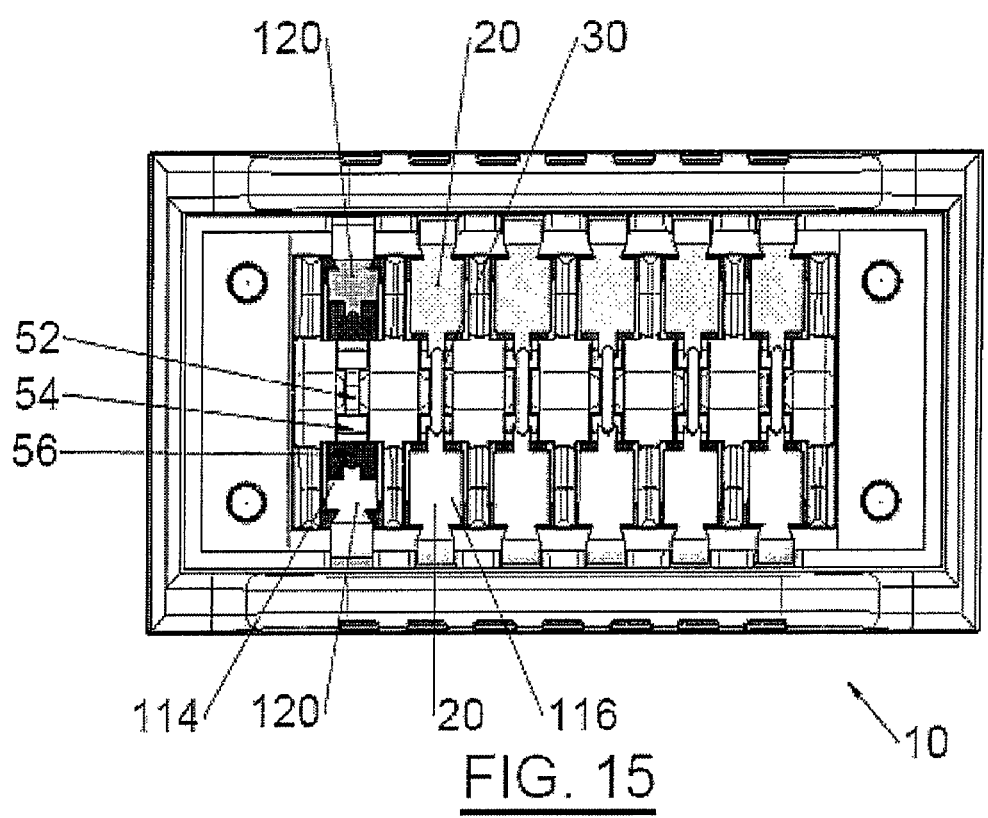
FIG. 15 is a top view of a hemostatic clip cartridge made in accordance with teachings of the present disclosure, the hemostatic clip cartridge with one hemostatic clip removed.

To highlight the dramatic difference in the level of visual indication provided, take a quick look at both FIG. 14 and FIG. 15. While black and white drawings lose the visual impact that is provided by selective use of contrasting colors, the difference between the FIG. 14 and FIG. 15 is striking. In each case, one of the six hemostatic clips 30 is removed from the container (Peiffer '447 hemostatic clip holder 210 in FIG. 14 and hemostatic clip cartridge 10 in FIG. 15). Note that the difference is not attributed to scale as the two drawings have been sized to be approximately the same scale (as evident from the length of the hemostatic clips 30).

As noted above, the Peiffer retaining fingers are adapted to return to their original position after being moved by the applicator jaw 18 (FIG. 1) during the process of loading a hemostatic clip 30 into the applicator 16 (FIG. 1). Thus, the pair of retaining fingers 222 in individual compartment 224 after removal of the hemostatic clip 30 from individual compartment 224 look the same as the pair of retaining fingers 220 in individual compartment 226 which still has a hemostatic clip 30. This results in very little visual difference between individual compartments with and without hemostatic clips 30. The lack of a pronounced visual difference is a user nuisance as a surgeon that is using many hemostatic clips 30 in a surgical procedure cannot be expected to count the number of hemostatic clips used and remember how many individual compartments have been harvested. So as the surgeon moves focus from the patient's body to the hemostatic clip holder 210 to obtain another hemostatic clip 30, it is desirable for the process of identifying which individual compartments have a hemostatic clip 30 to be as easy as possible.

In marked contrast, a hemostatic clip cartridge 10 in accordance with teachings of the present disclosure has a pronounced visual difference between the retained pair of retaining fingers 120 in individual compartment 114 after removal of the hemostatic clip as compared to adjacent individual compartment 116 that has the pair of retaining fingers 20 in the original position indicating to those glancing from afar that a hemostatic clip 30 has not yet been removed from individual compartment 116.

If the process of assembly is well controlled, then it would be rare if ever that an individual compartment did not receive a hemostatic clip 30 during assembly so that the position of the retaining fingers 20 would be effectively an indication that a hemostatic clip 30 remains in the individual compartment 116 available for loading into an applicator 16 (FIG. 1). Note that the visual indication is enhanced if the color or other aspects of the appearance of the applier sub-compartment 54 and the locking sub-compartment 56 are markedly different from the color and appearance of the retaining fingers 120. In order to provide at least a muted indication of the potential impact of a different color, the exposed portion of the visible table viewed through the bottoms of individual compartment 114 in FIG. 15 has been made dark. (As indicated in the cross section in FIG. 9 and in other drawings, the bottom is not solid.) The amount of visible table in FIG. 14 is so small that the drawing has not been made dark to show the small increase in the amount of table visible through the prior art hemostatic clip holder 210.

Returning to a comparison of FIG. 14 to FIG. 15, it can be seen that the increase in size between the hemostatic clip holder 210 and the hemostatic clip cartridge 10 in order to hold the same quantity of hemostatic clips 30 allows much larger compartments and larger retaining fingers (20 and 120). Notice that the width of the majority of each retaining finger (20 and 120) is several times wider than the width of the hemostatic clips 30. In this context, the width of the hemostatic clip 30 is the dimension orthogonal to the long axis of the compartment. As shown in FIG. 15, the width of the majority of each retaining finger 120 may be significantly more than the width of the hemostatic clip 30. This added width helps amplify the visual impact when retaining fingers are left in a position that indicates that the hemostatic clip 30 for that compartment has been harvested.

While the visual indication is increased if the width of the majority of the retaining finger is several times the width of the hemostatic clip, other narrower configurations such will provide some of the same type of visual indication.

An alternative way of describing the relationship of widths is to say that the hemostatic clip cartridge has a maximum width of the retaining finger that is more than 2.5 times the width of the centered clip-sub-compartment, (taking the widths orthogonal to the length of the individual compartment).

Figure 16A:
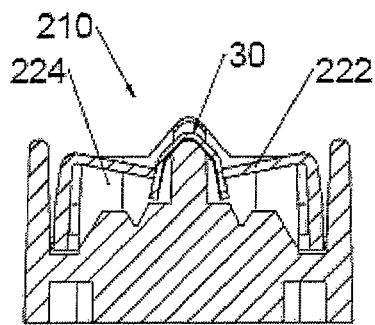
FIGS. 16A and 16B show a cross section of a prior art Peiffer type hemostatic clip holder before and after the removal of a hemostatic clip.
Figure 16B:
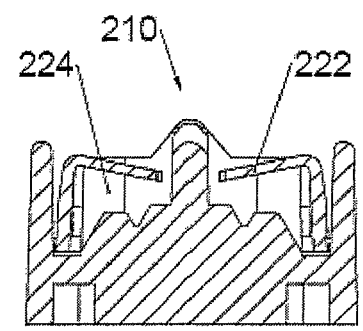

A comparison of FIGS. 16 and 17 helps reinforce the differences between a hemostatic clip cartridge 10 made in accordance with teachings of the present disclosure. FIG. 16A shows a section of a Peiffer hemostatic clip holder 210 before the removal of the hemostatic clip 30 from individual compartment 224. The distal ends of the pair of retaining fingers 222 are above the hemostatic clip 30. FIG. 16B shows the same cross section after the removal of the hemostatic clip 30 by the insertion of the hemostatic clip into the applicator 16 (not shown here). Notice that the position of the pair of retaining figures 222 is essentially the same before and after the removal of the hemostatic clip 30 so the position of the pair of retaining fingers 222 cannot be part of the visual indication that the hemostatic clip 30 has been removed from a particular individual compartment 224.

Figure 17A:
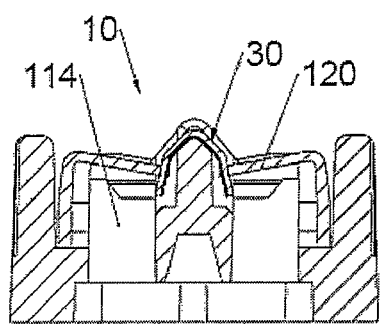
FIGS. 17A and 17B show a cross section of a hemostatic clip cartridge as shown in FIG. 15 before and after the removal of a hemostatic clip.
Figure 17B:
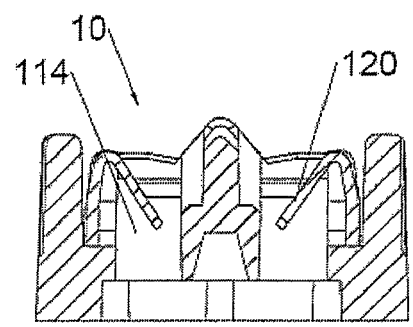

In contrast, FIG. 17A shows a section of a hemostatic clip cartridge 10 before the removal of the hemostatic clip 30 from individual compartment 114. The distal ends of the pair of retaining fingers 120 are above the hemostatic clip 30. FIG. 17B shows the same cross section after the removal of the hemostatic clip 30 by the insertion of the hemostatic clip into the applicator 16 (not shown here). Notice that the position of the pair of retaining figures 120 is markedly different before and after the removal of the hemostatic clip 30 so the position of the pair of retaining fingers 120 can play an important part of the visual indication that the hemostatic clip 30 has been removed from a particular individual compartment 114. The aggregate effect is that the view from above will change with the removal of a hemostatic clip 30 to decrease the visible area of the retaining fingers 120 with a corresponding increase in the visible area of the exposed bottom of the individual compartment 114.

Alternatives

One of ordinary skill in the art will appreciate that one general teaching of the present disclosure is that it is advantageous to have a cartridge for a set of hemostatic clips that changes the configuration of components within an individual compartment during the process of retrieving a hemostatic clip from that individual compartment to provide a non-subtle visual indication that the hemostatic clip has been harvested from that individual compartment. A specific set of components was described in great detail in the figures and associated text set forth above. One of ordinary skill in the art will recognize that other arrangements of components could be used to achieve this same end. A few of the possibilities are listed below to illustrate the point.

A designer could choose to add a feature (such as a slot, notch or groove) to the retaining fingers where each retaining finger contacts the locking tabs and allows the retaining finger to flex inward during applicator insertion and clear the locking tabs and then flex back to create an interference with the locking tab upon applicator removal so that the retaining finger is kept below the locking tabs.

A designer could choose to fabricate the retaining fingers out of a compliant material which would compress and pass past the locking tabs during applicator insertion of the applicator into the individual compartment but would then expand out to create an interference with the locking tab upon applicator removal to retain the retaining finger below the locking tab.

A designer could choose to fabricate the locking tabs out of a compliant material which would compress and allow the retaining finger to pass past the locking tabs during applicator insertion of the applicator into the individual compartment but the locking tabs would then expand out to create an interference with the retaining finger upon applicator removal to retain the retaining finger below the locking tab.

A designer could create flexible or hinged locking tabs that flex or otherwise move out of the way when the retaining finger as the retaining finger is forced down by applicator, but then returns to back to the original location after the retaining finger passes the interference point to create an interference for the retaining finger when the retaining finger attempts to return to the original location of the retaining finger. Again the net effect is that the retaining finger is held by the locking tabs in a position that is different from the original position to highlight the removal of the hemostatic clip from that particular individual compartment.

A designer could add a feature (such as a slot, notch or groove) or make other design modifications to the retaining finger so that the retaining finger is permanently deformed during the process of the applicator depressing the retaining finger during the harvesting of a hemostatic clip. If the permanent deformation is sufficient to preclude the return of the retaining finger to its original position, then the retaining finger may provide a significant visual indication that the hemostatic clip has been removed from that particular individual compartment even in the absence of locking tabs to hold the retaining finger. A designer may choose to use a combination of a permanent deformation of the retaining finger combined with interference from a locking tab to hold the retaining finger in a position after hemostatic clip harvest that is different than the position of the retaining finger before harvesting the hemostatic clip.

A designer would not have to implement symmetric locking tabs. For example, a designer could choose to add a single locking tab with a top feature (i.e. angle, slope, or cam) that extends into the individual compartment so that during applicator insertion the downward movement of the retaining finger deflects the retaining finger to an off-centered opening allowing the retaining finger to pass the locking tab. Upon applicator retraction, the bottom of the locking tab creates an interference with the retaining finger as the retaining finger moves back towards the centerline of the individual compartment. In the re-centered position, the retaining finger can not pass the single locking tab and lacks a force input to move the retaining finger off-center to get past the locking tab.

Any of the above-mentioned alternates could employ a "catch" feature on either the retaining finger, the locking tab or both to increase the retention characteristics of the interference created between the retaining finger and the locking tab.

Any of the above-mentioned alternates could employ one or multiple locking tabs.

While the designs discussed above implied that the sidewalls were rigid and did not flex or otherwise deform appreciably, a designer could rely on the side walls to flex or otherwise deform to allow the retaining finger to pass the locking tabs or could rely on the flexing or other form of elastic deformation of the side walls as a portion of the movement required to allow the retaining finger to get below the interference from the locking tabs. Another option is that the shape of at least one compartment locking tab deforms during the insertion of the clip applicator into that individual compartment to harvest the hemostatic clip.

While the implementations described above use an interaction between the retaining finger wings (element 68 in FIG. 5B) and the locking tabs protruding from the side walls, other interactions could be used to retain the retaining finger in a post-harvest position.

Figure 18:
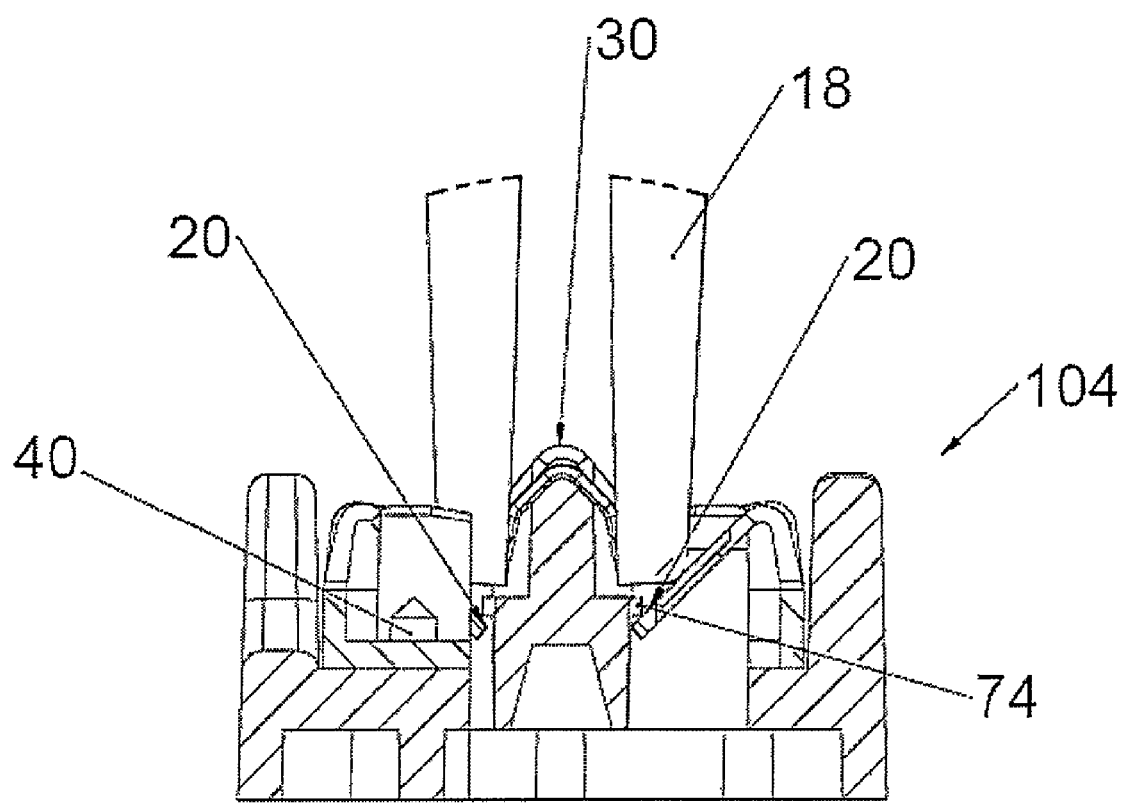
FIG. 18 is a section end view of an alternative implementation of a cartridge showing an applicator fully inserted into the cartridge and depressing retaining fingers below platform tabs 74, the view in FIG. 18 showing the contrast with this implementation and the one shown in FIG. 12 showing a section taken through the line A-A of FIG. 8.

FIG. 18 shows a cartridge 104 via an analogous cross section to that shown in FIG. 12 in order to facilitate comparison with FIG. 12. In FIG. 18, the distal ends of the retaining fingers 20 are moved downward in the cartridge 104 by the downward movement of the applicator jaws 18 as the applicator jaws 18 are inserted to harvest a hemostatic clip 30. The downward applicator force provided by the user to insert the applicator jaws 18 into the cartridge and over the hemostatic clip 30 pushes the retaining finger 20 past the platform tabs 74. After the applicator jaws 18 are removed from the cartridge 104 along with the harvested hemostatic clip 30, the depressed retaining fingers 20 cannot resume their pre-harvesting position as platform tabs 74 prevent the return to the pre-harvesting position.

While having each of the pair of retaining fingers 20 engage with a platform tab 74 to retain the retaining finger in a post-harvest position would give more visual impact than having merely one of the pair of retaining fingers 20 be so retained, one could implement teachings of the present disclosure by having only one of the two retaining fingers 20 retained.

In many implementations using platform tabs 74 the extent of the interference between the platform tab 74 and the at least one retaining finger 20 will cause a discernable bump as the at least one retaining finger 20 passes beyond the one or more platform tabs 74 to provide feedback to the user that the applicator jaws 18 are fully inserted and thus the hemostatic clip 30 should be engaged with the applicator jaws 18 and the at least one retaining finger 20 will be retained in the post-harvest position.

The various implementations illustrated or discussed above have pushed retaining fingers 20 beyond a point and the hemostatic clip cartridge has one or more features that prevent at least some of the retaining fingers from returning to their pre-harvest position. Thus, while the retaining finger 20 is free to move downward, it is restrained from moving back to the pre-harvest position. An alternative is that as the distal ends of the retaining fingers 20 are moved downward in the cartridge 104 by the downward movement of the applicator jaws 18 as the applicator jaws 18 are inserted to harvest a hemostatic clip 30. The downward applicator force provided by the user to insert the applicator jaws 18 into the cartridge and over the hemostatic clip 30 pushes the retaining finger 20 to become wedged into a locked position by an engagement with the hemostatic clip cartridge 104. After the applicator jaws 18 are removed from the cartridge 104 along with the harvested hemostatic clip 30, the depressed retaining fingers 20 cannot resume their pre-harvesting position as one or more of the retaining fingers are wedged into the hemostatic clip cartridge.

Figure 19A:
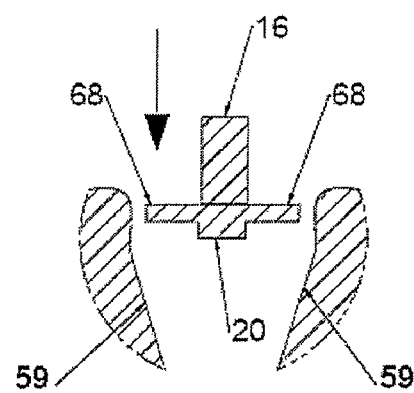
FIG. 19A, FIG. 19B and FIG. 19C show a section view of the retaining fingers 20 with respect to the wedge walls 59 before, during and after applicator insertion.
Figure 19B:
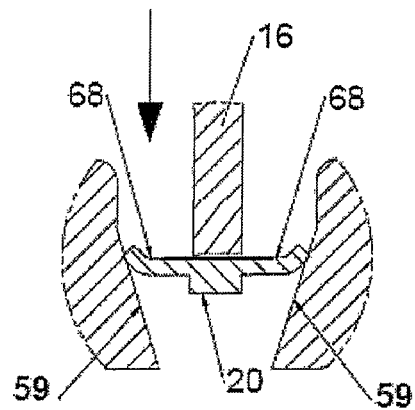
Figure 19C:
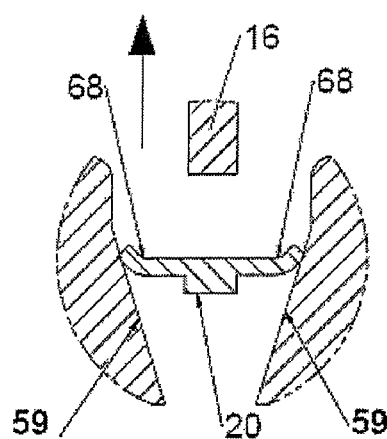

FIGS. 19A, 19B and 19C show a section view of the retaining fingers 20 with respect to the wedge walls 59 prior to, during and after applicator insertion (applicator is represented by the general element number 16 rather than using the applicator jaw element number 18). An example of the wedge concept is the use of compartment walls (wedge walls 59) that are not parallel with one another but slant inward so that the spacing between the walls decreases as the retaining finger 20 is moved downward until the spacing between the wedge walls 59 is less than the full width of the retaining finger 20. Further downward motion of the retaining finger 20 imposes a friction fit between the retaining finger 20 and the wedge walls 59.

While the examples given above implied that the base component (FIG. 1 element 12) is placed on a substantially horizontal surface and the applicator jaws (FIG. 1 element 18) move downward to harvest the hemostatic clip and leave the retaining finger (FIG. 1, element 20) in a depressed orientation relative to the starting orientation, this set of consistent orientation clues is meant to facilitate the provision of the teachings of the present disclosure and not to serve as a limitation. One of skill in the art will recognize that for example, if the hemostatic clip cartridge 10 using locking tabs was mounted on a vertical surface—that the same movements could be termed outward or away rather than down without changing the nature of the teaching. For an additional example, in an implementation using locking tabs, if for some reason the hemostatic clip cartridge was mounted on a horizontal surface above the surgeon, the applicator jaws would force the retaining fingers upward and they would be retained in an upward position above the locking tabs.

A designer of skill in the art will select one or more materials for creating the various components described above based upon the suitability of the material to be machined or formed into a particular shape, the required mechanical qualities of the component including the ability to deform or resist deformation, the ability to accept coloring or other appearance altering treatments; the ability to withstand any chosen sterilization process (if any process is selected), and any other qualities important to the designer.

Teachings May be Used in Isolation or in Combination.

One of skill in the art will recognize that some of the alternative implementations set forth above are not universally mutually exclusive and that in some cases additional implementations can be created that employ aspects of two or more of the variations described above. Additional variations may be created by implementing some but not all of the teachings provided for a particular implementation provided above. Likewise, the present disclosure is not limited to the specific examples provided to promote understanding of the various teachings of the present disclosure.

Having thus described a presently preferred embodiment of the present disclosure, it will now be appreciated that the present disclosure has conveyed improvements over the prior art, and it will be understood by those skilled in the art that many changes in construction and widely differing embodiments and applications of the various teachings of the present disclosure will suggest themselves without departing from the spirit and scope of the present disclosure. The disclosures and the description herein are intended to be illustrative and are not in any sense limiting of the legal scope of protection sought. The legal limitations of the scope of the claimed invention are set forth in the claims that issue based upon this disclosure and extend to cover their legal equivalents. Those unfamiliar with the legal tests for equivalency should consult a person registered to practice before the patent authority which granted this patent such as the United States Patent and Trademark Office or its counterpart.

What is claimed is:

1. An improved hemostatic clip cartridge for storing and dispensing hemostatic clips which are preformed into a proper shape for engagement by a clip applicator, the hemostatic clip cartridge comprising:
   a plurality of individual compartments, each of the individual compartments comprising:
   a pair of compartment side walls, and
   a pedestal for loosely supporting a hemostatic clip; and
   retaining means for retaining a hemostatic clip in each of the individual compartments comprising:
      a pair of fingers extending into each of the individual compartments wherein each of the fingers has a contacting end that contacts the hemostatic clip, and a groove formed in the contacting end of each of the fingers; whereby the groove maintains the hemostatic clip centered in the individual compartment;
   wherein the improvement comprises:
   laterally extending compartment locking tabs protruding into the individual compartment from each compartment side wall and finger locking tabs extending laterally from each finger towards each compartment side wall,
   the compartment locking tabs and finger locking tabs adapted for engagement such that force imparted by the clip applicator during engagement of a hemostatic clip by the clip applicator causes a movement of the finger locking tabs past the compartment locking tabs but subsequent removal of the force imparted by the clip applicator as the clip applicator is removed with the engaged hemostatic clip does not cause reversal of the movement of the finger locking tabs past the compartment locking tabs;
   whereby a user may look at the position of the pair of fingers in a particular individual compartment as an indicator of whether the clip applicator has already been inserted into that individual compartment.

2. The improved hemostatic clip cartridge of claim 1 wherein the finger locking tabs are an integral part of the corresponding finger but have a reduced material thickness relative to a longitudinal centerline of the finger.

3. The improved hemostatic clip cartridge of claim 1 wherein at least one of the finger locking tabs flexes relative to a longitudinal centerline of the finger in order to move at least one of the finger locking tabs past the compartment locking tabs.

4. The improved hemostatic clip cartridge of claim 1 wherein the hemostatic clip cartridge has received a set of hemostatic clips, one hemostatic clip per individual compartment.

5. The improved hemostatic clip cartridge of claim 4 wherein the hemostatic clip cartridge loaded with at least one hemostatic clip is sterilized for use in surgery.

6. The improved hemostatic clip cartridge of claim 1 wherein each individual compartment has a clip sub-compartment having a first average width sufficiently narrow to limit the position of the hemostatic clip, an applier sub-compartment with a second average width, wider than the first average width but sufficiently narrow to help guide the clip applicator as the clip applicator is inserted into the individual compartment, and a locking sub-compartment with a third average width, wider than the second average width with adequate room for movement of the finger locking tabs past the compartment locking tabs in response to the force imparted by the clip applicator during engagement of the hemostatic clip.

7. The improved hemostatic clip cartridge of claim 1 wherein the hemostatic clip cartridge provides tactile feedback to the user as a distal end of at least one finger locking tab goes from flexed to un-flexed as the finger locking tab passes beyond a compartment locking tab.

8. A hemostatic clip cartridge for storing and dispensing hemostatic clips which are harvested from individual compartments by a clip applicator, the hemostatic clip cartridge comprising:
    at least one individual compartment for holding a hemostatic clip until harvested by a clip applicator, each individual compartment comprising:
        a pair of compartment side walls,
        a clip sub-compartment for loosely supporting the hemostatic clip;
        an applier sub-compartment for guiding the clip applicator;
        a pair of retaining fingers in a first position before the hemostatic clip is harvested from that individual compartment, each retaining finger having a first end and a clip retaining end, the first end attached to the hemostatic clip cartridge and the clip retaining end contacting the hemostatic clip contained in that individual compartment before the hemostatic clip is harvested by the clip applicator, the pair of retaining fingers helping to maintain the hemostatic clip in the hemostatic clip cartridge, and
        at least one compartment locking tab preventing at least one of the pair of retaining fingers from returning to approximately the first position after the hemostatic clip is harvested from that individual compartment so that at least one of the pair of retaining fingers is in a post-harvest position which provides a visual indication that the clip applicator has accessed that individual compartment.

9. The hemostatic clip cartridge of claim 8 wherein at least one of the pair of retaining finger is pushed past a pair of compartment locking tabs, one compartment locking tab on each sidewall by an insertion of the clip applicator into that individual compartment to harvest the hemostatic clip.

10. The hemostatic clip cartridge of claim 8 wherein a shape of at least one compartment locking tab deforms during an insertion of the clip applicator into that individual compartment to harvest the hemostatic clip.

11. The hemostatic clip cartridge of claim 8 wherein the individual compartment has the clip sub-compartment having a first average width sufficiently narrow to limit the position of the hemostatic clip, the applier sub-compartment with a second average width, wider than the first average width but sufficiently narrow to help guide the clip applicator as the clip applicator is inserted into that individual compartment, and a locking compartment with a third average width, wider than the second average width with adequate room for the operation of a means for preventing at least one of the pair of retaining fingers from returning to approximately the first position after the hemostatic clip is harvested from that individual compartment.

12. The hemostatic clip cartridge of claim 11 wherein a maximum width of the retaining finger is more than 2.5 times a width of clip sub-compartment, wherein the widths are measured orthogonal to a length of the individual compartment.

13. The hemostatic clip cartridge of claim 11 wherein the retaining finger has a wide section for a majority of the retaining finger and a width of the wide section of the retaining finger is more than triple a width of the hemostatic clip as measured orthogonal to a length of the individual compartment.

14. The hemostatic clip cartridge of claim 8 wherein the movement of at least one of the pair of retaining fingers from the first position towards the post-harvest position provides tactile feedback to a user that the at least one of the pair of retaining fingers has moved such that the retaining finger will be maintained in a post-harvest position indicating that the hemostatic clip has been accessed by the clip applicator.

15. A hemostatic clip cartridge for storing and dispensing hemostatic clips which are harvested from individual compartments by a clip applicator, the hemostatic clip cartridge comprising:
    at least one individual compartment for holding a hemostatic clip until harvested by a clip applicator, each individual compartment comprising:
        a pair of compartment side walls,
        a clip sub-compartment for loosely supporting the hemostatic clip;
        an applier sub-compartment for guiding the clip applicator;
        at least one laterally extending compartment locking tab protruding into the individual compartment from at least one of the pair of compartment side walls,
        a pair of retaining fingers in a first position before the hemostatic clip is harvested from that individual compartment, each retaining finger having a first end and a clip retaining end, the first end attached to the hemostatic clip cartridge and the clip retaining end contacting the hemostatic clip contained in that individual compartment before the hemostatic clip is harvested by the clip applicator, the pair of retaining fingers helping to maintain the hemostatic clip in the hemostatic clip cartridge, and
    wherein a shape of at least one of the pair of compartment side walls elastically deforms during an insertion of the clip applicator into that individual compartment to harvest the hemostatic clip to allow at least one of the pair of retaining fingers past at least one compartment locking tab, but subsequent removal of the clip applicator from that individual compartment with the engaged hemostatic clip does not cause a movement of the at least one of the pair of retaining fingers past the at least one compartment locking tab so that at least one of the pair of retaining fingers is in a post-harvest position which provides a visual indication that the clip applicator has accessed that individual compartment.

16. The hemostatic clip cartridge of claim 15 wherein the movement of at least one of the pair of retaining fingers from the first position towards the post-harvest position provides tactile feedback to a user that the at least one of the pair of retaining fingers has moved such that the retaining finger will be maintained in the post-harvest position indicating that the hemostatic clip has been accessed by the clip applicator.

* * * * *